United States Patent [19]

De Lacharriere et al.

[11] Patent Number: 5,968,532

[45] Date of Patent: *Oct. 19, 1999

[54] USE OF AN ETHYLENEDIAMINE DERIVATIVE IN A COSMETIC OR DERMATOLOGICAL COMPOSITION CONTAINING IN PARTICULAR A PRODUCT HAVING AN IRRITANT SIDE EFFECT

[75] Inventors: Oliver De Lacharriere, Paris; Jean-Baptiste Galey, Aulnay-Sous-Bois; Lionel Breton, Versailles; Jacqueline Dumats, Villepinte, all of France

[73] Assignee: Societe L'Oreal S.A., Paris, France

[ * ] Notice: This patent is subject to a terminal disclaimer.

[21] Appl. No.: 08/977,061

[22] Filed: Nov. 24, 1997

Related U.S. Application Data

[62] Division of application No. 08/575,089, Dec. 19, 1995, Pat. No. 5,714,155.

[30] Foreign Application Priority Data

Dec. 19, 1994 [FR] France ................................. 9415250

[51] Int. Cl.⁶ .................................................. A61K 7/48
[52] U.S. Cl. ..................... 424/401; 514/844; 514/846; 514/937; 514/938; 514/944
[58] Field of Search ........................... 424/401; 514/844, 514/846, 937, 938, 944

[56] References Cited

U.S. PATENT DOCUMENTS 5,521,220  5/1996  O'Neill et al. ........................ 514/649

FOREIGN PATENT DOCUMENTS

| 0375668 | 6/1990 | European Pat. Off. . |
| 0522808 | 1/1993 | European Pat. Off. . |
| 0653208 | 5/1995 | European Pat. Off. . |
| 93/10073 | 5/1993 | WIPO . |
| 94/11338 | 5/1994 | WIPO . |

*Primary Examiner*—Jyothsna Venkat
*Attorney, Agent, or Firm*—Burns, Doane, Swecker & Mathis, L.L.P.

[57] ABSTRACT

The invention relates to the use of an ethylenediamine derivative as a substance P antagonist and/or as a local analgesic in, or for the preparation of, a cosmetic or dermatological composition for treating sensitive skin-types. The invention relates in particular to the use of this derivative for preventing and/or combating skin irritations and/or dartres and/or erythema and/or dysaesthesic sensations and/or sensations of inflammation and/or pruritus of the skin and/or the mucous membranes including the eyes. The invention also relates to a composition containing a product having an irritant side effect and this derivative, so as to reduce this irritant effect or even to remove it altogether.

12 Claims, No Drawings

USE OF AN ETHYLENEDIAMINE DERIVATIVE IN A COSMETIC OR DERMATOLOGICAL COMPOSITION CONTAINING IN PARTICULAR A PRODUCT HAVING AN IRRITANT SIDE EFFECT

This application is a divisional of application Ser. No. 08/575,089, filed Dec. 19, 1995 now U.S. Pat. No. 5,714,155.

The present invention relates to the use of an ethylenediamine derivative as a substance P antagonist and/or as a local analgesic in or for the preparation of a cosmetic, pharmaceutical or dermatological composition, intended for the treatment of sensitive skin-types, as well as to a cosmetic, pharmaceutical or dermatological composition containing this derivative for the purpose of reducing or removing altogether the irritant effects of certain products such as active agents used in the above fields.

It is known that some skin-types are more sensitive than others. However, the symptoms of sensitive skin-types were poorly characterized hitherto and the problem of these skin-types was, as a result, poorly defined; nobody knew the exact process involved in skin sensitivity. Some thought that a sensitive skin was a skin which reacted to cosmetic products, while others thought that it concerned a skin which reacted to several external factors, not necessarily associated with cosmetic products.

Certain tests have been tried in order to attempt to define sensitive skin-types, for example tests using lactic acid and DMSO which are known to be irritant substances: see for example the article by K. Lammintausta et al., Dermatoses, 1988, 36, pages 45–49; and the article by T. Agner and J. Serup, Clinical and Exerimental Dermatology, 1989, 14, pages 214–217. However, these tests did not make it possible to characterize sensitive skin-types.

Moreover, sensitive skin-types were likened to allergic skin-types.

On account of the ignorance of the characteristics of sensitive skin-types, it was hitherto very difficult or even impossible to treat them. Indeed, they were treated indirectly, for example by limiting, in the cosmetic or dermatological compositions, the use of products with an irritant nature, such as surfactants, preserving agents or perfumes, as well as the use of certain cosmetic or dermatological active agents.

After many clinical tests, the Applicant has been able to determine the symptoms associated with sensitive skin-types. These symptoms are in particular subjective signs, which are essentially dysaesthesic sensations. The term dysaesthesic sensations refers to more or less painful sensations experienced in an area of skin, such as stinging, tingling, itching or pruritus, burning, inflammation, discomfort, pulling, etc.

The Applicant has in addition been able to demonstrate that a sensitive skin-type is not an allergic skin-type. Indeed, an allergic skin-type is a skin-type which reacts to an external agent, an allergen, which triggers an allergic reaction. This is an immunological process which takes place only when an allergen is present and which affects only sensitized individuals. On the contrary, the essential characteristic of sensitive skin, according to the Applicant, is a mechanism of response to external factors, which may concern any individual, even if the individuals said to have sensitive skin react faster thereto than the other individuals. This is a nonspecific mechanism and not an immunological one.

The Applicant has now found that sensitive skin-types can be split into two major clinical forms; irritable and/or reactive skin-types and intolerant skin-types.

An irritable and/or reactive skin-type is a skin-type which reacts by a pruritus, that is to say by itching, or by stinging, to various factors such as the environment, emotions, foods, the wind, rubbing, shaving, soap, surfactants, hard water with a high calcium concentration, temperature variations or wool. In general, these signs are associated with a dry skin with or without dartres, or with a skin which displays an erythema.

An intolerant skin-type is a skin-type which reacts, by sensations of inflammation, pulling, tingling and/or redness, to various factors such as the environment, emotions, foods and certain cosmetic products. In general, these signs are associated with a hyperseborrhoeic or acneic skin-type with or without dartres, and with an erythema.

"Sensitive" scalps have a more unequivocal clinical semeiology: the sensations of pruritus and/or of stinging and/or of inflammation are essentially triggered by local factors such as rubbing, soap, surfactants, hard water with a high calcium concentration, shampoos or lotions. These sensations are also sometimes triggered by factors such as the environment, emotions and/or foods. Erythema and hyperseborrhoea of the scalp and the presence of dandruff are often associated with the above signs.

Moreover, in certain anatomical regions such as the major folds (groin, genital, axillary, popliteal, anal and submammary regions, and in the fold of the elbows) and the feet, sensitive skin is reflected in pruriginous sensations and/or dysaesthesic sensations (inflammation, stinging) associated in particular with sweat, rubbing, wool, surfactants, certain cosmetic preparations, hard water with a high calcium concentration and/or temperature variations.

The Applicant has also developed a test in order to determine whether or not a skin-type is sensitive. Indeed, after having carried out a great many tests with the aim of defining sensitive skin, the Applicant has found, surprisingly, that there is a connection between individuals with sensitive skin and those who react to a topical application of capsaicin.

The capsaicin test consists in applying, to about 4 $cm^2$ of skin, 0.05 ml of a cream containing 0.075% of capsaicin and in noting the appearance of subjective signs induced by this application, such as stinging, burning and itching. In individuals having sensitive skin, these signs appear between 3 and 20 minutes after the application and are followed by the appearance of an erythema which starts at the edge of the zone of application.

Hitherto, capsaicin was used as a medicinal product, in particular for treating zona pains. Capsaicin induces a release of neuropeptides, and in particular of tachykinins, which originate from epidermal and dermal nerve endings. The Applicant has observed that the physiopathological pattern common to all the conditions of sensitive skin-types was associated with a great ability to release tachykinins, and more particularly substance P, into the skin. The dysaesthesic manifestations which are induced by their release are referred to as being "neurogenic".

This substance P is a polypeptide chemical component produced and released by a nerve ending. It forms part of the tachykinin family. Substance P is involved in particular in the transmission of pain and in central nervous system complaints such as anxiety, schizophrenia, in respiratory and inflammatory diseases, in gastrointestinal diseases, in rheumatic diseases and in certain dermatological diseases such as eczema.

The Applicant has now discovered that the essential characteristic of sensitive skin-types is associated with the release of substance P and thus that the use of substance P antagonists could allow a preventive and/or curative effect to be obtained for sensitive skin-types.

In order to treat sensitive skin-types, the Applicant has thus envisaged using substance P antagonists. Indeed, it has been observed by the Applicant, surprisingly, that the incorporation of a substance P antagonist into a cosmetic, pharmaceutical or dermatological composition makes it possible to avoid the irritation of and/or dysaesthesic sensations in and/or pruritus of the skin.

Ethylenediamine derivatives which may be used as substance P antagonists in pharmaceutical compositions for the treatment and prevention of central nervous system disorders are known from document WO 93/10073. These compounds have the drawback of often being difficult to manufacture or to formulate in a cosmetic, pharmaceutical or dermatological composition. Moreover, this document neither describes nor suggests the use of some of these derivatives in compositions for topical application.

Certain ethylenediamine derivatives which may be used in the treatment and prevention of sunburn are known from document EP-A-653,208. However, this document neither describes nor suggests the use of these derivatives in compositions for topical application for the treatment of sensitive skin-types.

The object of the present invention is thus the use of at least one compound of formula (I) below or one of the cosmetically, dermatologically or pharmaceutically acceptable salts thereof, as a substance P antagonist in, or for the preparation of, a cosmetic, dermatological or pharmaceutical composition for treating sensitive skin-types:

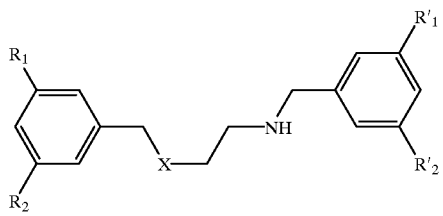

$R_1$ and $R_2$ are, independently of each other, H, —$CH_3$, —$OCH_3$, —$CF_3$, CN, —$NO_2$, a halogen atom $R'_1$ and $R'_2$ are, independently of each other, —$CH_3$. —$OCH_3$, —$CF_3$, —CN, —$NO_2$, a halogen atom X represents O or NH.

X preferably represents NH. In particular, the compound of formula (I) is chosen from N,N'-bis(3,5-dimethylbenzyl) ethylenediamine and N,N'-bis(3,5-dimethoxybenzyl) ethylenediamine.

The salts of the compounds of formula (I) are, in particular, the hydrochlorides, the sulphates, the phosphates, the acetates and the carbonates.

A further object of the present invention is the use of at least one compound of formula (I) above as a local analgesic in, or for the preparation of, a cosmetic, pharmaceutical or dermatological composition for the treatment of sensitive skin-types.

A further object of the present invention is the use of at least one compound of formula (I) above in, or for the preparation of, a cosmetic, pharmaceutical or dermatological composition for preventing and/or combating skin irritations and/or dartres and/or erythema and/or inflammation sensations and/or dysaesthesia and/or pruritus of the skin and/or the mucous membranes.

The composition of the invention contains a cosmetically, pharmaceutically or dermatologically acceptable medium, that is to say a medium which is compatible with tissues, mucous membranes, the skin, the nails and the hair. Thus, the composition containing one or more compounds of formula (I) may be injected, ingested or applied to the face, the neck, the hair and the nails, the major folds or any other area of body skin, and the mucous membranes (buccal, jugal, gingival, genital or conjunctive mucosae).

In order for a substance to be recognized as a substance P antagonist, it must comply with the following characteristics:

have a selective affinity for the NK1 receptors of tachykinins, have a pharmacological antagonist activity towards substance P, that is to say induce a coherent pharmacological response in at least one of the following two tests:

the antagonist substance must reduce the extravasation of plasma across the vascular wall induced by capsaicin or by antidromic nerve stimulation, or alternatively the antagonist substance must induce an inhibition of the smooth muscle contraction induced by the administration of substance P.

The compounds of formula (I) or the salts thereof do indeed satisfy these conditions.

No one had hitherto established a connection between substance P and sensitive skin. The clinical signs of sensitive skin are essentially subjective: stinging, tingling, pruritus, pulling and inflammation, and they are occasionally associated with erythema. These signs are due to nonspecific external factors. The symptoms appear to be essentially localized on the face, the neck and the scalp, but may also appear on the entire body.

Advantageously, the compounds of formula (I) or the salts thereof are combined with products having an irritant side effect, used commonly in the cosmetic, pharmaceutical or dermatological field and more especially cosmetic, pharmaceutical or dermatological active agents. The presence of a substance P antagonist of formula (I), in particular one which is salified, in a cosmetic, pharmaceutical or dermatological composition containing a product having an irritant effect makes it possible to attenuate this irritant effect considerably, or even to remove it altogether. It makes it possible in particular to increase the amount of active agent having an irritant effect relative to the amount of active agent normally used, for the purpose of increasing the effectiveness.

Thus, a further subject of the invention is a cosmetic, pharmaceutical or dermatological composition containing, in a cosmetically or pharmaceutically acceptable medium, at least one product having an irritant side effect, characterized in that it also contains at least one compound of formula (I) above, which may be salified.

Another object of the present invention is the use of at least one compound of formula (I) above or one of the cosmetically, pharmaceutically or dermatologically acceptable salts thereof in, or for the preparation of, a cosmetic, pharmaceutical or dermatological composition containing at least one product having an irritant side effect, in order to reduce this irritant effect and/or to remove it altogether.

In particular, the products having an irritant side effect are chosen from surfactants (ionic or nonionic surfactants), preserving agents, organic solvents, or active agents such as α-hydroxy acids (citric, malic, glycolic, tartaric, mandelic or lactic acid), β-hydroxy acids (salicylic acid and derivatives thereof), α-keto acids, β-keto acids, retinoids (retinol, retinal and retinoic acid), anthralins (dioxyanthranol), anthranoids, peroxides (in particular benzoyl peroxide), minoxidil, lithium salts, antimetabolites, vitamin D and derivatives thereof, hair dyes or toners (para-phenylenediamine and derivatives thereof, and aminophenols), perfumed alcoholic solutions (fragrances, eaux de toilette, aftershave and deodorants), antiperspirants (certain aluminium salts), active agents for depilation or permanent-waving (thiols), and depigmenting active agents (hydroquinone).

The use of substance P antagonist makes it possible in particular to multiply by 2 to 10 times the amount of active agent having an irritant side effect compared with the state of the art, without experiencing all of the discomforts mentioned above. Thus, it is possible to use hydroxy acids at up to 50% of the weight of the composition, or retinoids at up to 5%, without any discomfort.

In the compositions of the invention, the compound of formula (I) or one of the salts thereof may be used as a substance P antagonist and/or as a local analgesic, preferably in an amount ranging from 0.000001 to 5% by weight relative to the total weight of the composition, and in particular in an amount ranging from 0.0001 to 0.1% by weight relative to the total weight of the composition.

The compositions of the invention may be in all the pharmaceutical forms normally used, depending on whether the composition must be ingested, injected or applied to the skin or the mucous membranes.

For topical application, the composition must in particular take the form of an aqueous or oily solution or a dispersion of the lotion or serum type, emulsions of liquid or semi-liquid consistency of the milk type, obtained by dispersion of a fatty phase in an aqueous phase (O/W) or conversely (W/O), or suspensions or emulsions of smooth consistency of the aqueous or anhydrous cream or gel type, or alternatively microcapsules or microparticles, microemulsion, or vesicle dispersions of ionic and/or nonionic type. These compositions are prepared according to the usual methods.

They may also be used for the hair in the form of aqueous, alcoholic or aqueous-alcoholic solutions, or in the form of creams, gels, emulsions or mousses or alternatively in the form of aerosol compositions also containing a propellant under pressure.

For injection, the composition may be in the form of an aqueous or oily lotion or in the form of serum. For the eyes, it may be in the form of drops, and for ingestion it may be in the form of capsules, granules, syrups or tablets.

The amounts of the various constituents of the compositions according to the invention are those conventionally used in the fields considered.

These compositions constitute in particular cleansing, protective, treatment or care creams for the face, for the hands, for the feet, for the major anatomical folds or for the body (for example day creams, night creams, make-up-removing creams, foundation creams and sun creams), fluid foundations, make-up-removing milks, body milks for care or protection, sun milks, skin care lotions, gels or mousses such as cleansing lotions, antisun lotions, artificial tanning lotions, compositions for the bath, deodorizing compositions containing a bactericide, aftershave gels or lotions, hair-removing creams, compositions to counter insect bites, pain-relief compositions, and compositions for treating certain skin diseases such as eczema, rosacea, psoriasis, lichens and severe pruritus.

The compositions according to the invention may also consist of solid preparations constituting cleansing bars or soaps.

The compositions may also be packaged in the form of an aerosol composition also containing a propellant under pressure.

The compound of the invention may also be incorporated into various haircare compositions, and in particular shampoos, hairsetting lotions, treating lotions, styling creams or gels, dye compositions (in particular oxidation dyes) optionally in the form of colouring shampoos, restructuring lotions for the hair, permanent-wave compositions (in particular compositions for the first stage of a permanent-waving operation), lotions or gels for combating hair loss, antiparasitic shampoos, and the like.

The compositions of the invention may also be for buccodental use, for example a toothpaste. In this case, the compositions may contain adjuvants and additives which are usual for compositions for buccal use and, in particular, surfactants, thickeners, wetting agents, polishing agents such as silica, various active ingredients such as fluorides, in particular sodium fluoride, and optionally sweeteners such as sodium saccharinate.

When the composition of the invention is an emulsion, the proportion of the fatty phase may range from 5% to 80% by weight, and preferably from 5% to 50% by weight, relative to the total weight of the composition. The oils, the waxes, the emulsifiers and the coemulsifiers used in the composition in emulsion form are chosen from those used conventionally in the cosmetics field. The emulsifier and the coemulsifier are present in the composition at a proportion ranging from 0.3% to 30% by weight, and preferably of from 0.5 to 20% by weight, relative to the total weight of the composition. The emulsion may also contain lipid vesicles.

When the composition of the invention is an oily solution or gel, the fatty phase may represent more than 90% of the total weight of the composition.

In a known manner, the cosmetic composition of the invention may also contain adjuvants which are common in the cosmetics field, such as hydrophilic or lipophilic gelling agents, hydrophilic or lipophilic additives, preserving agents, antioxidants, solvents, fragrances, fillers, screening agents, odour absorbers and dyestuffs. The amounts of these various adjuvants are those used conventionally in the cosmetics field and, for example, from 0.01 % to 10 % of the total weight of the composition. Depending on their nature, these adjuvants may be introduced into the fatty phase, into the aqueous phase and/or into the lipid spherules.

As oils or waxes which may be used in the invention, there may be mentioned mineral oils (liquid petrolatum), plant oils (liquid fraction of karite butter, sunflower oil), animal oils (perhydrosqualene), synthetic oils (purcellin oil), silicone oils or waxes (cyclomethicone) and fluoro oils (perfluoropolyethers), beeswaxes, carnauba wax or paraffin wax. Fatty alcohols and fatty acids (stearic acid) may be added to these oils.

As emulsifying agents which may be used in the invention, there may be mentioned for example glyceryl stearate, polysorbate 60 and the PEG-6/PEG-32/glycol stearate mixture sold under the name Tefose® 63 by the company Gattefosse.

As solvents which may be used in the invention, there may be mentioned lower alcohols, in particular ethanol and isopropanol, and propylene glycol.

Hydrophilic gelling agents which may be mentioned are carboxyvinyl polymers (carbomer), acrylic copolymers such as acrylate/alkylacrylate copolymers, polyacrylamides, polysaccharides such as hydroxypropyl cellulose, natural gums and clays, and, as lipophilic gelling agents, there may be mentioned modified clays such as bentones, fatty acid metal salts such as aluminium stearates, and hydrophobic silica, ethyl cellulose and polyethylene.

The composition of the invention may contain other hydrophilic active agents such as proteins or protein hydrolysates, amino acids, polyols, urea, allantoin, sugars and sugar derivatives, water-soluble vitamins, plant extracts and hydroxy acids.

Lipophilic active agents which may be used are retinol (vitamin A) and derivatives thereof, tocopherol (vitamin E) and derivatives thereof, essential fatty acids, ceramides, essential oils, and salicylic acid and derivatives thereof.

It is possible, inter alia, to combine the compound of formula (I), which is optionally salified, with other active agents intended in particular for the prevention and/or treatment of skin complaints. Among these active agents, there may be mentioned by way of example:

agents which modify cutaneous differentiation and/or proliferation and/or pigmentation such as retinoic acid and isomers thereof, retinol and esters thereof, vitamin D and derivatives thereof, oestrogens such as oestradiol, kojic acid or hydroquinone;

antibacterial agents such as clindamycin phosphate, erythromycin or antibiotics from the tetracycline family;

antiparasitic agents, in particular metronidazole, crotamiton or pyrethroids;

antifungal agents, in particular compounds belonging to the imidazole family such as econazole, ketoconazole or miconazole or salts thereof, polyene compounds such as amphotericin B, compounds from the allylamine family such as terbinafine, or alternatively octopirox;

steroidal anti-inflamatory agents such as hydrocortisone, betamethasone valerate or clobetasol propionate, or nonsteroidal anti-inflaoatory agents such as ibuporofen and salts thereof, diclofenac and salts thereof, acetylsalicylic acid, acetaminophen or glycyrrhetinic acid;

anaesthetics such as lidocaine hydrochloride and derivatives thereof;

antipruriginous agents such as thenaldine, trimeprazine or cyproheptadine;

antiviral agents such as acyclovir;

keratolytic agents such as alpha- and beta-hydroxycarboxylic acids or beta-ketocarboxylic acids, the salts, amides or esters thereof and more particularly hydroxy acids such as glycolic acid, lactic acid, salicylic acid, citric acid and fruit acids in general, and 5-n-octanoylsalicylic acid;

anti-free-radical agents such as alpha-tocopherol or esters thereof, superoxide dismutases, certain metal chelating agents or ascorbic acid and esters thereof;

antiseborrhoeic agents such as progesterone;

antidandruff agents such as octopirox or zinc pyrithione;

antiacne agents such as retinoic acid or benzoyl is peroxide.

A further subject of the present invention is a cosmetic treatment process, characterized in that a composition as described above, containing at least one compound of formula (I) or one of the cosmetically acceptable salts thereof in a cosmetically acceptable medium, is applied to the skin, to the hair and/or to the mucous membranes.

The cosmetic treatment process of the invention may be carried out in particular by applying the cosmetic or hygiene compositions as defined above, according to the usual technique for the use of these compositions. For example: application of creams, gels, sera, lotions, make-up-removing milks or antisun compositions to the skin or to dry hair, application of a hair lotion to wet hair, application of shampoo, or alternatively application of toothpaste to the gums.

The compounds of the invention may be prepared as described in document WO 94/11338 filed in the name of the Applicant. In this application, the compounds of formula (I) are presented as synthetic intermediates. These compounds are advantageously prepared in only two steps. The general synthetic scheme is given below:

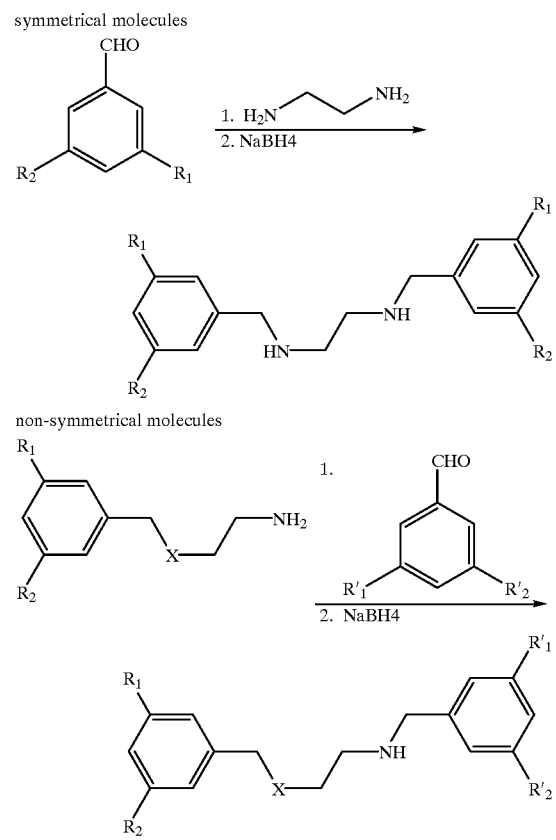

The following examples and compositions illustrate the invention. In the compositions, the proportions indicated are percentages by weight.

EXAMPLE 1

Synthesis of N,N'-bis(3,5-dimethylbenzyl)ethylenediamine

This compound corresponds to $R_1$, $R_2$, $R'_1$, $R'_2$=—$CH_3$ and X=NH.

First Step 5.0 g of 3,5-dimethylbenzaldehyde are dissolved in 50 ml of methanol at room temperature in a 100 ml three-necked flask. The mixture is heated to 50° C. and 1.25 ml of ethylenediamine are added. It is then left to cool to room temperature. The reaction medium rapidly becomes heterogeneous with precipitation of a white solid. The product is collected by filtration on a sinter funnel, washed copiously with cold methanol and then dried under vacuum in a desiccator to give 4.6 g of diimine (yield=85%).

Characterization $^1$H NMR: δ (ppm): 2.41 (s, 12H) ; 3.97 (s, 4H) ; 7.20 (s, 2H); 7.44 (s, 4H); 8.38 (s, 2H).

Second Step 5.45 g of the diimine are suspended in 50 ml of absolute ethanol at room temperature in a 250 ml three-necked flask. 1.10 g of sodium borohydride pellets are then added and the mixture is stirred at room temperature for 15 h. The medium is then concentrated under reduced pressure, followed by hydrolysis with about 50 ml of aqueous 6N HCl solution to pH<1. A precipitate forms rapidly. The mixture is then cooled to +5° C. for about 1 h with gentle stirring. The precipitate is filtered off on a sinter funnel and washed with 50 ml of ice-cold water before being dried under vacuum in a desiccator. The solid is then resuspended in 200 ml of ethyl ether and stirred for 2 h at room temperature. The solid is filtered off and 4.0 g of N,N'-bis(3,5-dimethylbenzyl) ethylenediamine dihydrochloride are recovered (yield= 58%).

Characterization $^1$H NMR (DMSO-d$_6$): δ (ppm): 2.13 (s, 12H); 3.04 (s, 4H); 3.86 (s, 4H); 6.87 (s, 2H); 7.01 (s, 4H); 8.69 (s, 2H).

EXAMPLE 2

Synthesis of N,N'-bis(3,5-dimethoxybenzyl) ethylenediamine

This compound corresponds to $R_1$, $R_2$, $R'_1$, $R'_2$=—OCH$_3$ and X=NH.

N,N'-Bis(3,5-dimethoxybenzyl)ethylenediamine dihydrochloride is prepared according to the same process as for Example 1.

Characterization $^1$H NMR (DMSO-d$_6$): δ (ppm): 3.36 (s, 4H); 3.76 (s, 12H); 4.12 (s, 4H); 6.52 (dd, 2H); 6.82 (d, 4H); 9. 88 (bs, 4H).

Pharmacological activity of the compounds of Examples 1 and 2 a). Receptor binding to human NK1 receptor according to the technique described by Heuillet et al., J. Neurochem. 60: 868–76 (1993):
  57% binding for the compound of Example 1 at a concentration of 10 μM
  23% binding for the compound of Example 2 at a concentration of 10 μM b). Model of antagonism of the in vitro contraction of guinea pig ileum by substance P (10 nM) according to the technique described by Dion et al., Life Sci. 41: 2269–78 (1987) and Patacchini et al., Eur. J. Pharmacol. 215: 93–8 (1992).

| concentration | 1 μM | 10 μM | 100 μM |
| --- | --- | --- | --- |
| compound of Example 1 | | | |
| % inhibition of contraction | −24% | −92% | −100% |

These tests clearly show that the compounds of Examples 1 and 2 are indeed substance P antagonists.

Composition 1: Make-up-removing lotion for the face

| | |
| --- | --- |
| Compound of Example 1 | 5.00 |
| Antioxidant | 0.05 |
| Isopropanol | 40.00 |
| Preserving agent | 0.30 |
| Water | qs 100% |

Composition 2: Facial care gel

| | |
| --- | --- |
| Compound of Example 2 | 0.05 |
| Hydroxypropyl cellulose (Klucel H sold by the company Hercules) | 1.00 |
| Antioxidant | 0.05 |
| Isopropanol | 40.00 |
| Preserving agent | 0.30 |
| Water | qs 100% |

Composition 3: Facial care cream (oil-in-water emulsion)

| | |
| --- | --- |
| Hydrochloride of the compound of Example 2 | 0.02 |
| Glyceryl stearate | 2.00 |
| Polysorbate 60 (Tween 60 sold by the company ICI) | 1.00 |
| Stearic acid | 1.40 |
| Triethanolamine | 0.70 |
| Carbomer | 0.40 |
| Liquid fraction of karite butter | 12.00 |
| Perhydrosqualene | 12.00 |
| Antioxidant | 0.05 |
| Fragrance | 0.5 |
| Preserving agent | 0.30 |
| Water | qs 100% |

Composition 4: Shampoo

| | |
| --- | --- |
| Sulphate of the compound of Example 1 | 0.02 |
| Hydroxypropyl cellulose (Klucel H sold by the company Hercules) | 1.00 |
| Fragrance | 0.50 |
| Preserving agent | 0.30 |
| Water | qs 100% |

Composition 5: Anti-wrinkle care cream for the face (oil/water emulsion)

| | |
| --- | --- |
| Compound of Example 1 | 0.15 |
| Glyceryl stearate | 2.00 |
| Polysorbate 60 (Tween 60 sold by the company ICI) | 1.00 |
| Stearic acid | 1.40 |
| 5-n-Octanoylsalicylic acid | 0.50 |
| Triethanolamine | 0.70 |
| Carbomer | 0.40 |
| Liquid fraction of karite butter | 12.00 |
| Perhydrosqualene | 12.00 |
| Antioxidant | 0.05 |
| Fragrance | 0.5 |
| Preserving agent | 0.30 |
| Water | qs 100% |

Composition 6: Pain-relief gel

| | |
| --- | --- |
| Compound of Example 2 | 0.03 |
| Hydroxypropyl cellulose (Klucel H sold by the company Hercules) | 1.00 |
| Antioxidant | 0.05 |
| Lidocaine hydrochloride | 2.00 |
| Isopropanol | 40.00 |
| Preserving agent | 0.30 |
| Water | qs 100% |

Composition 7: Solar erythema care cream (oil-in-water emulsion)

| | |
| --- | --- |
| Compound of Example 1 | 0.25 |
| Glyceryl stearate | 2.00 |
| Polysorbate 60 (Tween 60 sold by the company ICI) | 1.00 |
| Stearic acid | 1.40 |

-continued

| | |
|---|---|
| Glycyrrhetinic acid | 2.00 |
| Triethanolamine | 0.70 |
| Carbomer | 0.40 |
| Liquid fraction of karite butter | 12.00 |
| Sunflower oil | 10.00 |
| Antioxidant | 0.05 |
| Fragrance | 0.5 |
| Preserving agent | 0.30 |
| Water | qs 100% |

Composition 8: Gel for the treatment of acne

| | |
|---|---|
| Compound of Example 2 | 5.00 |
| All-trans-retinoic acid | 0.05 |
| Hydroxypropyl cellulose (Klucel H) | 1.00 |
| Antioxidant | 0.05 |
| Isopropanol | 40.00 |
| Preserving agent | 0.30 |
| Water | qs 100% |

Composition 9: Lotion for removing acne scars

| | |
|---|---|
| Compound of Example 1 | 5.00 |
| Glycolic acid | 50.00 |
| Hydroxypropyl cellulose (Klucel H) | 0.05 |
| NaOH | qs pH = 2.8 |
| Preserving agent | 0.30 |
| Ethanol | qs 100% |

We claim:

1. A composition for cosmetic, pharmaceutical or dermatological usage which comprises at least one product having an irritant side effect and further comprising at least one compound of Formula (I) set forth below, or a cosmetically, pharmaceutically or dermatologically acceptable salt thereof:

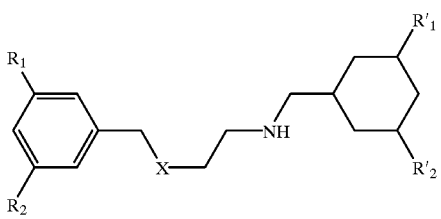

wherein $R_1$ and $R_2$ may be the same or different and are selected from the group consisting of H, —CH$_3$, —OCH$_3$, —CF$_3$, CN, —NO$_2$, and a halogen atom and R'$_1$ and R'$_2$ may be the same or different and are selected from the group consisting of —CH$_3$, —OCH$_3$, —CF$_3$, —CN, —NO$_2$, and a halogen atom, and X is O or NH, and wherein said product and said compound of Formula (I) or a cosmetically, pharmaceutically or dermatologically acceptable salt thereof are contained in a cosmetically or pharmaceutically or dermatologically acceptable medium, wherein said at least one product having the irritant side effect is contained in an amount which would otherwise cause irritation in the absence of an anti-irritant effective amount of said at least one compound of Formula (I), wherein said product having an irritant side effect is selected from the group consisting of α-hydroxy acids, β-hydroxy acids, α-keto acids, β-keto acids, retinoids, anthralins, anthranoids, peroxides, minoxidil, lithium salts, antimetabolites, vitamin D, hair dyes, hair toners, antiperspirants, depilatory agents, permanent-waving agents, perfumed alcoholic solutions, depigmenting agents, surfactants and solvents.

2. The composition of claim 1, wherein X is NH.

3. The composition according to claim 1, wherein said compound is contained in an amount ranging from 0.000001 to 5% by weight relative to the total weight of the composition.

4. The composition according to claim 2, wherein said compound is contained in an amount ranging from 0.000001 to 5% by weight relative to the total weight of the composition.

5. The composition according to claim 1, wherein the compound is contained in an amount ranging from 0.0001 to 0.1% by weight relative to the total weight of the composition.

6. The composition according to claim 1, wherein said product having an irritant side effect is a cosmetically, pharmaceutically or dermatologically active agent.

7. The composition according to claim 1, which further comprises at least one agent selected from the group consisting of antibacterial agents, antiparasitic agents, antifungal agents, antiviral agents, anti-inflammatory agents, antipruriginous agents, anesthetics, keratolytic agents, anti-free-radical agents, antiseborrhoeic agents, antidandruff agents, antiacne agents, agents which modify cutaneous differentiation, agents which modify proliferation, and agents which modify pigmentation.

8. The composition according to claim 1, wherein said cosmetically or pharmaceutically or dermatologically acceptable medium is selected from the group consisting of aqueous, aqueous-alcoholic solutions, water-in-oil emulsions, oil-in-water emulsions, microemulsions, aqueous gels, anhydrous gels, serums and dispersions of vesicles.

9. The composition according to claim 1, where in the compound of Formula (I), $R_1$, $R_2$, R'$_1$ and R'$_2$ are each —CH$_3$ and X is NH.

10. The composition according to claim 1, where in the compound of Formula (I), $R_1$, $R_2$, R'$_1$ and R'$_2$ are each —OCH$_3$ and X is NH.

11. The composition according to claim 1, wherein said compound having an irritant side effect is a retinoid.

12. The composition of claim 1, wherein said at least one compound of Formula (I) is N,N'-bis(3,5-dimethylbenzoyl) ethylene diamine or N,N'-bis(3,5-dimethoxybenzoyl) ethylene diamine.

* * * * *